US00PP15983P2

(12) United States Plant Patent
Sakazaki

(10) Patent No.: US PP15,983 P2
(45) Date of Patent: Sep. 20, 2005

(54) ***VERBENA* PLANT NAMED 'USBENA361'**

(50) Latin Name: *Verbena hybrida*
Varietal Denomination: USBENA361

(75) Inventor: Ushio Sakazaki, Shiga (JP)

(73) Assignee: Plant 21 LLC, San Marco, CA (US)

( * ) Notice: Subject to any disclaimer, the term of this patent is extended or adjusted under 35 U.S.C. 154(b) by 26 days.

(21) Appl. No.: 10/835,577

(22) Filed: Apr. 29, 2004

(51) Int. Cl.[7] ..... A01H 5/00
(52) U.S. Cl. ..... Plt./308
(58) Field of Search ..... Plt./308

*Primary Examiner*—Anne Marie Grunberg
(74) *Attorney, Agent, or Firm*—C. A. Whealy

(57) ABSTRACT

A new and distinct cultivar of *Verbena* plant named 'USBENA361', characterized by its low and outwardly spreading plant habit; vigorous growth habit; numerous large white-colored flowers; and resistance to Powdery Mildew.

1 Drawing Sheet

Botanical classification/cultivar designation: *Verbena hybrida* cultivar USBENA361.

BACKGROUND OF THE INVENTION

The present Invention relates to a new and distinct cultivar of *Verbena* plant, botanically known as *Verbena hybrida*, and hereinafter referred to by the name 'USBENA361'.

The new *Verbena* is a product of a planned breeding program conducted by the Inventor in Hikone, Shiga, Japan. The objective of the breeding program is to develop new disease-resistant and high temperature-tolerant *Verbena* cultivars with semi-upright plant habit and attractive flower coloration.

The new *Verbena* originated from a cross-pollination made by the Inventor on May 5, 2000 of a proprietary selection of *Verbena hybrida* identified as code number VJL24-2, not patented, as the female, or seed, parent with a proprietary selection of *Verbena hybrida* identified as code number VJL22-1, not patented, as the male, or pollen, parent. The cultivar USBENA361 was discovered and selected by the Inventor as a flowering plant within the progeny from the aforementioned cross-pollination in a controlled environment in Bonsall, Calif. on Jun. 24, 2001.

Asexual reproduction of the new cultivar by cuttings at Bonsall, Calif., since Jun. 27, 2001, has shown that the unique features of this new *Verbena* are stable and reproduced true to type in successive generations of asexual reproduction.

SUMMARY OF THE INVENTION

The following traits have been repeatedly observed and are determined to be the unique characteristics of 'USBENA361'. These characteristics in combination distinguish 'USBENA361' as a new and distinct cultivar:

1. Low and outwardly spreading plant habit.
2. Vigorous growth habit.
3. Numerous large white-colored flowers.
4. Resistant to Powdery Mildew.

In side-by-side comparisons conducted in Hikone, Shiga, Japan, plants of the new *Verbena* differed from plants of the female parent selection in the following characteristics:

1. Plants of the new *Verbena* were not as upright as plants of the female parent selection.
2. Plants of the new *Verbena* were more vigorous than plants of the female parent selection.
3. Plants of the new *Verbena* flowered earlier than plants of the female parent selection.

In side-by-side comparisons conducted in Hikone, Shiga, Japan, plants of the new *Verbena* differed from plants of the male parent selection in the following characteristics:

1. Plants of the new *Verbena* were more upright than plants of the male parent selection.
2. Plants of the new *Verbena* were resistant to Powdery Mildew whereas plants of the male parent selection were susceptible to Powdery Mildew.

The new *Verbena* can be compared to the cultivar, Sunmaref TPPW, not patented. However, in side-by-side comparisons conducted in Bonsall, Calif., plants of the new *Verbena* differed from plants of the cultivar Sunmaref TPPW in the following characteristics:

1. Plants of the new *Verbena* were more vigorous than plants of the cultivar Sunmaref TPPW.
2. Plants of the new *Verbena* were more freely flowering than plants of the cultivar Sunmaref TPPW.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately descibed the colors of the new *Verbena*.

The photograph at the bottom of the sheet comprises a side perspective view of a typical plant of 'USBENA361' grown in a container.

The photograph at the top of the sheet is a close-up view of typical flowers of 'USBENA361'.

DETAILED BOTANICAL DESCRIPTION

In the following description, color references are made to The Royal Horticultural Society Colour Chart, 1995 Edition, except where general terms of ordinary dictionary significance are used. Plants grown in 15-cm containers were used for the aforementioned photographs and following description. Plants had been growing for about ten weeks when the photographs and the description were taken. Plants were grown under conditions which closely approximate commercial production conditions during the winter in Bonsall, Calif. in a polyethylene-covered greenhouse. During the production period, day temperatures ranged from about 13 to about 35° C. and night temperatures ranged from about 10 to about 16° C.

Botanical classification:

*Verbena hybrida* cultivar USBENA361.

Parentage:

*Female parent*.—Proprietary selection of *Verbena hybrida* identified as code number VJL24-2, not patented.

*Male parent*.—Proprietary selection of *Verbena hybrida* identified as code number VJL22-1, not patented.

Propagation:

*Type cutting*.—Vegetative tip cuttings.

*Time to initiate roots*.—About 7 days at 18° C.

*Time to develop roots*.—About 21 days at 18° C.

*Root description*.—Fibrous; whitish in color.

*Rooting habit*.—Freely branching.

Plant description:

*General appearance*.—Low and outwardly spreading plant habit; eventually somewhat trailing plant habit.

*Growth and branching habit*.—Freely basal branching; about ten lateral branches develop per plant. Pinching, that is, removal of the terminal apices, enhances branching with lateral branches potentially forming at every node. Vigorous growth habit; moderate growth rate.

*Plant height*.—About 15 cm.

*Plant diameter or spread*.—About 42 cm.

*Lateral branch description*.—Length: About 24 cm. Diameter: About 3 mm. Internode length: About 3 cm. Texture: Pubescent. Color: 146A.

*Foliage description*.—Arrangement: Opposite, simple. Length: About 2.8 cm. Width: About 2.4 cm. Shape: Deltoid. Apex: Broadly acute. Base: Attenuate. Margin: Deeply dissected. Texture, upper surface: Pubescent; slightly coarse. Texture, lower surface: Glabrous; slightly coarse. Venation pattern: Pinnate. Color: Developing and fully expanded foliage, upper surface: 147A. Developing and fully expanded foliage, lower surface: 147B. Venation, upper and lower surfaces: 147B. Petiole: Length: About 1.5 cm. Diameter: About 2 mm. Texture, upper and lower surfaces: Pubescent. Color, upper and lower surfaces: 147B.

Flower description:

*Flower type and habit*.—Single upright salverform flowers arranged on hemispherical corymbs. Freely flowering with about 50 flowers per inflorescence. Inflorescences positioned above and beyond the foliage. Flowers last about one week under greenhouse conditions. Corollas not persistent. Flowers not fragrant.

*Flowering season*.—In the garden, flowering is continuous from spring until fall.

*Inflorescence height*.—About 3.5 to 4 cm.

*Inflorescence diameter*.—About 4.5 cm.

*Flower size*.—Diameter: About 1.6 cm. Height (depth): About 2 cm.

*Flower buds*.—Length: About 1.5 cm. Diameter: About 3 mm. Shape: Elongate. Color: 155D.

*Petals*.—Quantity/arrangement: Five per flower fused at base. Lobe length: About 7 mm. Lobe width: About 6 mm. Shape: Cordate. Apex: Emarginate. Margin: Entire. Texture, upper and lower petal surfaces: Glabrous, smooth; velvety. Texture, throat and tube: Pubescent. Color: When opening, upper and lower surfaces: 155D. Fully opened, upper and lower surfaces: More white than 155D. Throat: 155D. Tube: 155D.

*Sepals*.—Quantity/arrangement: Five, fused into an elongated tube. Length: About 1 cm. Diameter: Less than 1 mm. Shape: Linear. Apex: Acuminate. Margin: Entire. Texture, upper and lower surfaces: Pubescent. Color, upper and lower surfaces: 146A.

*Peduncles*.—Length: About 6.8 cm. Diameter: About 2 mm. Strength: Strong. Angle to stem: Curving upright. Texture: Pubescent. Color: 146A.

*Reproductive organs*.—Stamens: Quantity: Four per flower. Anther shape: Oval. Anther length: Less than 1 mm. Anther color: 145C. Pollen amount: Scarce. Pollen color: 4A. Pistils: Quantity: One per flower. Pistil length: About 1.5 cm. Style length: About 1.3 cm. Style color: 145D. Stigma shape: Bi-parted. Stigma color: 144A. Ovary color: 144A.

*Seed/fruit*.—Seed and fruit production has not been observed.

Disease/pest resistance:

Plants of the new *Verbena* have been observed to be resistant to Powdery Mildew. Plants of the new *Verbena* have not been observed to be resistant to other pathogens and pests common to *Verbena*.

Temperature tolerance:

Plants of the new *Verbena* have been observed to be tolerant to temperatures ranging from −4 to 40° C.

It is claimed:

1. A new and distinct cultivar of *Verbena* plant named 'USBENA361', as illustrated and described.

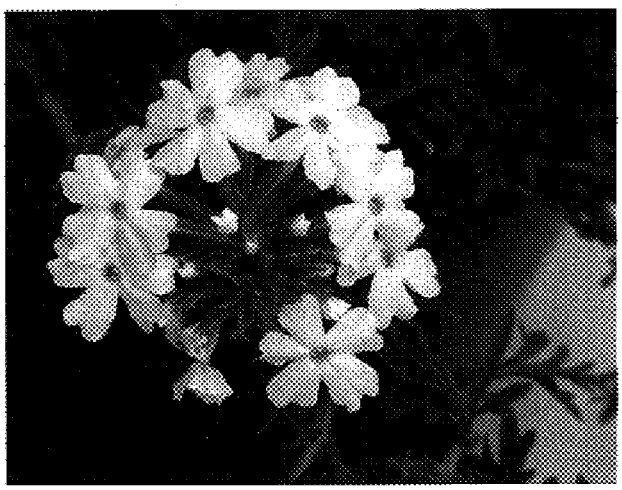
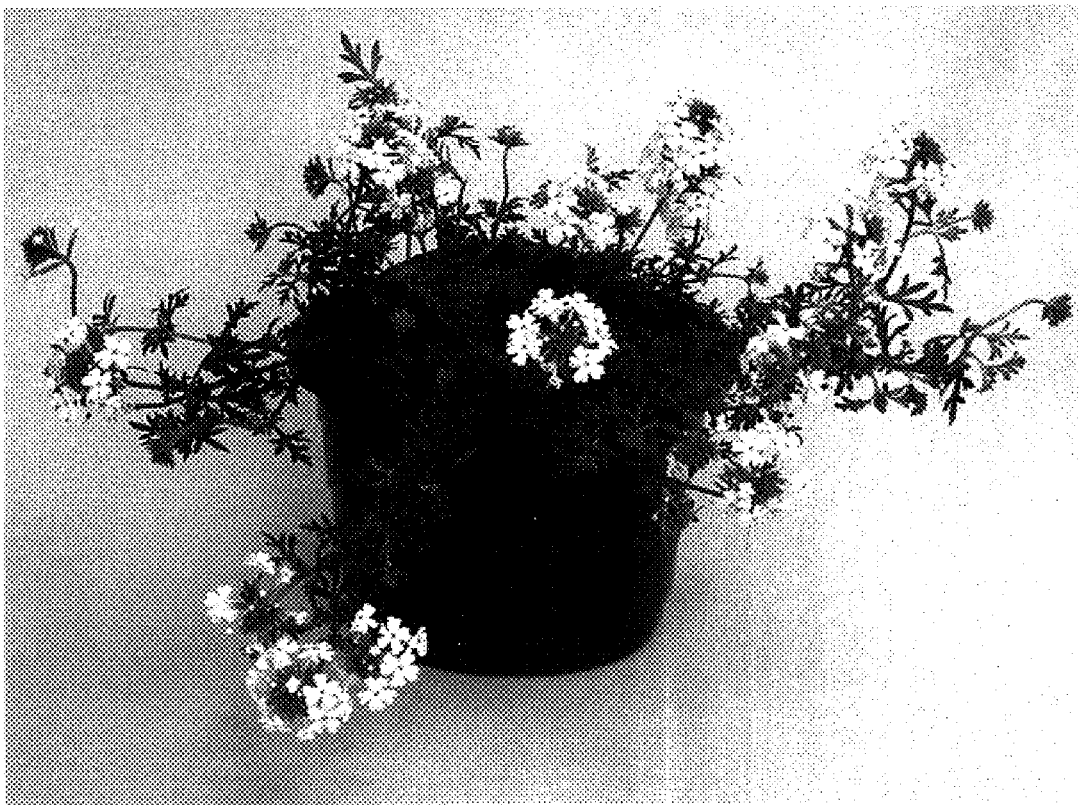

* * * * *